US008268342B2

(12) United States Patent
Panda et al.

(10) Patent No.: US 8,268,342 B2
(45) Date of Patent: Sep. 18, 2012

(54) BIODEGRADABLE POLYMER SCAFFOLD AND PROCESS FOR PREPARATION THEREOF

(75) Inventors: Amulya Kumar Panda, New Delhi (IN); Rajmohan Gopimohan, New Delhi (IN); Anish Chakkunkal, New Delhi (IN)

(73) Assignee: National Institute of Immunology (IN)

( * ) Notice: Subject to any disclaimer, the term of this patent is extended or adjusted under 35 U.S.C. 154(b) by 326 days.

(21) Appl. No.: 12/739,588

(22) PCT Filed: Oct. 23, 2008

(86) PCT No.: PCT/IN2008/000701
§ 371 (c)(1),
(2), (4) Date: Apr. 23, 2010

(87) PCT Pub. No.: WO2009/054006
PCT Pub. Date: Apr. 30, 2009

(65) Prior Publication Data
US 2010/0233277 A1    Sep. 16, 2010

(30) Foreign Application Priority Data
Oct. 26, 2007    (IN) .......................... 2248/DEL/2007

(51) Int. Cl.
*A61F 2/00*    (2006.01)
*A61K 9/14*    (2006.01)
*A61K 9/50*    (2006.01)
*C08G 63/08*    (2006.01)
*C12N 5/00*    (2006.01)
*C12N 5/02*    (2006.01)

(52) U.S. Cl. ........ 424/426; 424/489; 424/490; 424/491; 424/497; 528/354; 435/395; 435/396

(58) Field of Classification Search .................. 424/426, 424/489, 490, 491, 497; 528/354; 435/395, 435/396
See application file for complete search history.

(56) References Cited

U.S. PATENT DOCUMENTS
5,520,923 A * 5/1996 Tjia et al. ...................... 424/426

FOREIGN PATENT DOCUMENTS
WO    WO-9609078 A1    3/1996

OTHER PUBLICATIONS
"International Application No. PCT/IN2008/00701, International Search Report mailed Jan. 20, 2010", 4 pgs.
Jiang, Tao, et al., "In vitro evaluation of chitosan/poly(lactic acid-glycolic acie) sintered microsphere scaffolds for bone tissue engineering", *Biomaterials*, 27(28), (Oct. 2006).
Suciati, Tri, "Zonal release of proteins within tissue engineering scaffolds", *J Mater Sci: Mater Med.*, 17(11), (Nov. 2006), 1049-56.

\* cited by examiner

*Primary Examiner* — Blaine Lankford, Jr.
*Assistant Examiner* — Charles Zoltan Constantine
(74) *Attorney, Agent, or Firm* — Schwegman Lundberg & Woessner, P.A.

(57) ABSTRACT

The present invention relates to a process for preparation of a biodegradable polymer scaffold using biodegradable polymer, surfactant and alcohol. The biodegradable polymer scaffold obtained from the process disclosed is useful for tissue engineering, therapeutic compound delivery and/or wound dressing.

24 Claims, 6 Drawing Sheets

BIODEGRADABLE POLYMER SCAFFOLD AND PROCESS FOR PREPARATION THEREOF

PRIORITY CLAIM TO RELATED APPLICATIONS

This application is a national stage application under 35 U.S.C. §371 of PCT/IN2008/000701, filed Oct. 23, 2008, and published as WO 2009/054006 A2 on Apr. 30, 2009, which claims priority to Indian Application No. 2248/DEL/2007, filed Oct. 26, 2007, which applications and publication are incorporated herein by reference and made a part hereof in their entirety, and the benefit of priority is claimed thereto.

FIELD OF THE INVENTION

The present invention relates to biodegradable polymer membrane and/or scaffold useful for tissue engineering, drug delivery and/or wound dressing.

BACKGROUND OF THE INVENTION

Polylactic acid (PLA) and polylactic-co-glycolic acid (PLGA) are biodegradable polymers being extensively used for various biomedical applications especially as scaffold in the field of tissue engineering (Middleton J C, Tipton A J. Synthetic biodegradable polymers as orthopedic devices. Biomaterials 2000; 21: 2335-46; Papkov-Sokolsky M, Agashi K, Laya A, Shakesheff K, Domb A J. Polymer carrier for drug deliver and tissue engineering. Adv Drug Deliv Rev 2007; 59:187-206; Kohane D S, Langer R. Polymeric Biomaterials in Tissue Engineering. Pediatric Research 2008; 63: 487-91). Polymeric scaffolds serve as a physical support to provide cells with the appropriate three-dimensional architecture for in vitro cell culture as well as in vivo tissue regeneration (Langer R, Vacanti J P. Tissue Engineering. Science 1993; 260: 920-6; Griffith L G, Naughton G. Tissue engineering-current challenge and expanding opportunities. Science 2002; 295:1009-1014). Ideally, tissue engineering scaffolds formulated from biocompatible and bio-resorbable polymers like PLA should possess a well defined macrostructure and microstructure with controlled porous architecture to promote cell attachment and proliferation (Ma P X. Scaffold for tissue fabrication. Mater Today 2004; 7: 30-40; Nair L S, Laurencin C T. Polymers as biomaterials for tissue engineering and controlled drug delivery. Adv Biochem Eng/Biotechnol 2006; 102: 47-90; Chung H G and Park T G. Surface engineered and drug releasing pre-fabricated scaffolds for tissue engineering. Adv Drug Deliv Rev 2007; 59: 249-262). Apart from this, release of appropriate growth factors from the scaffold may promote controlled vascularization and tissue growth in three dimensions (Tabata Y. Significance of release technology in tissue engineering. Drug Discov Today 2005; 10: 1639-46; Biondi M, Ungaro F, Quaglia F, Netti P M. Controlled drug delivery in tissue engineering. Adv Drug Deliv Rev 2008; 60: 2229-42). Various methods like particulate leaching, emulsion freeze drying, phase inversion technique, solvent casting, electro spinning and thermal sintering have been employed to formulate scaffolds using PLA and PLGA for tissue engineering applications (Chung H G and Park T G. Surface engineered and drug releasing pre-fabricated scaffolds for tissue engineering. Adv Drug Deliv Rev 2007; 59: 249-262; Mikos A G et al. Preparation and characterization of poly (L-lactic acid) foams. Polymer 1994; 35: 1068-77; Hutmacher D W. Scaffold design and fabrication technologies for engineering tissues-state of the art and future perspectives. J Biomater Sci: Polym Ed 2001; 12: 107-24; Wu L, Jing D, Ding J. A "room-temperature" injection molding/particulate leaching approach for fabrication of biodegradable three-dimensional porous scaffolds. Biomaterials 2006; 27: 185-91; Ma P X. Biomimetic Materials for Tissue Engineering. Adv Drug Deliv Rev 2008; 60: 184-98; Shin M, Abukawa H, Troulis M J, Vacanti J P. Development of a biodegradable scaffold with interconnected pores by heat fusion and its application to bone tissue engineering. J Biomed Mater Res A 2008; 84(3): 702-9). PLA and PLGA nano fibers have also been used extensively as scaffold (Chen V J, Ma P X. Nano-fibrous poly (L-lactic acid) scaffolds with interconnected spherical macropores. Biomaterials 2004; 25: 2065-73; Liu X, Won Y, Ma P X. Porogen-induced surface modification of nano-fibrous poly(L-lactic acid) scaffolds for tissue engineering. Biomaterials 2006; 27: 3980-7; Guarino V, Causa F, Taddei P, Foggia M D, Ciapetti G, Martini D et al. Polylactic acid fibre-reinforced polycaprolactone scaffolds for bone tissue engineering. Biomaterials 2008; 29: 3662-70) and particularly for skin tissue engineering (Kumbar S G, Nukavarapu S P, James R, Nair L S, Laurencin C T. Electrospun poly (lactic acid-co-glycolic acid) scaffolds for skin tissue engineering. Biomaterials 2008; 29:4100-07; Zong X, Li S, Chen E, Garlick B, Kim K S, Fang D, et al. Prevention of post-surgery-induced abdominal adhesions by electrospun bioabsorbable nano-fibrous poly(lactide-co-glycolide)-based membranes. Ann Surg 2004; 240: 910-5) Particulate leaching method using different porogen is widely used to fabricate scaffolds but have problems of residual salts in the scaffold, irregularly shaped pores and poorly interconnected structures for three dimensional cell cultures (Mikos A G, Bao Y, Cima L G, Ingber D E, Vacanti J P, Langer R. Preparation of poly(glycolic acid) bonded fiber structures for cell attachment and transplantation. J Biomed Mater Res 1993; 27: 183-9). Wetting of polylactide particles or wafers transiently with an organic solvent like dichloromethane (DCM) to form scaffolds have also been tied (Mikos A G, Sarakinos G, Leite S M, Vacanti J P, Langer R. Laminated three-dimensional biodegradable foams for use in tissue engineering. Biomaterials 1993; 14: 323-30; Jaklenec A, Wan E, Murray M E, Mathiowitz E. Novel scaffolds fabricated from protein loaded microspheres for tissue engineering. Biomaterials. 2008; 29: 185-92). The disadvantage of such processes is that there is no control over the fusion process and prolonged exposure of polylactide particles to DCM results in loss of polymer particle characteristics. Labile biomolecules entrapped in the polymer scaffold also get denatured during interaction with organic solvent used for solubilization of the polymer.

Self-assembly is the organization of smaller units into regular three dimensional higher order structures without human intervention or involvement of external energy (Breen T L, Tien J, Oliver S R J, Hadzic T, Whitesides G M. Design and self-assembly of open, regular, 3D mesostructures. Science 1999; 284: 948-51; Whitesides G M, Grzybowski B. Self-assembly at all scales. Science 2002; 295: 2418-21; Capito R M, Azevedo H S, Velichko Y S, Mata A, Stupp S I. Self-Assembly of large and small molecules into hierarchically ordered sacs and membranes. Science 2008; 319: 1812-16). The classical example is the self-assembly of lipid molecules in nature into tubular microstructure (Schnur J M, Price R, Schoen P, Yager P, Calvert J M, Georger J, Singh A. Lipid-based tubule microstructures. Thin Solid Films 1987; 152: 181-206; Richard C, Balavoine F, Schultz P, Ebbesen T W, Mioskowski C. Supramolecular self-assembly of lipid derivatives on carbon nanotubes. Science 2003; 300: 775-78). Surfactant mediated self-assembly and synthesis of novel materials has been extensively investigated and utilized for various purposes including self assembly of nanoparticles in to higher order structure (Zemb Th, Dubois M, Demé B, Gulik-Krzywicki Th. Self-Assembly of flat nanodiscs in salt-free catanionic surfactant solutions. Science 1999; 283: 816-19; Inagaki S, Guan S, Ohsuna T, Terasaki O. An ordered mesoporous organosilica hybrid material with a crystal like wall structure. Nature 2002; 416: 304-07; Li M, Schnablegger H, Mann S. Coupled synthesis and self-assembly of nanoparticles to give structures with controlled organization. Nature 1993; 402: 393-95). Self-assembly of structures mediated by surfactant molecules tend to be mild, with little production of heat and friction and thus will be especially suited for biomedical applications. Scaffold made from self assembling peptide nano fiber has been reported to accelerate wound healing (Hartgerink J D, Beniash E, Stupp S I. Peptide-amphiphile nanofibers: A versatile scaffold for the preparation of self-assembling materials. Proc Nat Acad Sci 2002; 99: 5133-8; Schneider A, Grlick J A, Egles C. Self-assembling peptide nanofiber scaffolds accelerate wound healing. Plos ONE 2008; 3: e1410). However the major limitations of self-assembly of molecules into scaffolds are their inability to control pore size, lack of stable morphology and biodegradability of the scaffold.

SUMMARY OF THE INVENTION

The present invention provides a biodegradable polymer scaffold useful for tissue engineering, therapeutic compound delivery and/or wound dressing. The present invention further provides a process for the biodegradable polymer scaffold.

One aspect of the present invention is to provide a process of preparation of a biodegradable polymer scaffold useful for tissue engineering, therapeutic compound delivery and/or wound dressing, wherein the process comprises spreading surfactant coated polymer particles on a support; soaking the particles with alcohol; and washing with water to obtain the polymer scaffold.

Another aspect of the present invention is provides a process of preparation of a biodegradable polymer scaffold, wherein the process comprises spreading cetyl trimethyl ammonium bromide (CTAB) coated polymer particles of Poly-DL-lactide (PDLLA) on a support; soaking the particles with ethanol or methanol; and washing with water to obtain the polymer scaffold.

Yet another aspect of the present invention is to provide a process of preparation of a biodegradable polymer scaffold, wherein the process comprises spreading cetyl trimethyl ammonium bromide (CTAB) coated polymer particles of Poly lactide co-glycolide particle on a support; soaking the particles with ethanol or methanol; and washing with water to obtain the polymer scaffold.

In another aspect, the present invention provides a biodegradable polymer scaffold useful for tissue engineering, therapeutic compound delivery and/or wound dressing, wherein the scaffold is obtained by the process as disclosed in the present invention.

(A) Scanning electron microscopy (SEM) of PDLLA-CTAB particles prepared by solvent evaporation method before fusion (B) A digital image of a polymeric membrane after fusion of PDLLA-CTAB particles in presence of ethanol at room temperature (C and D) SEM pictures of PDLLA-CTAB particles after the process of fusion in the presence of ethanol.

Figure 2:
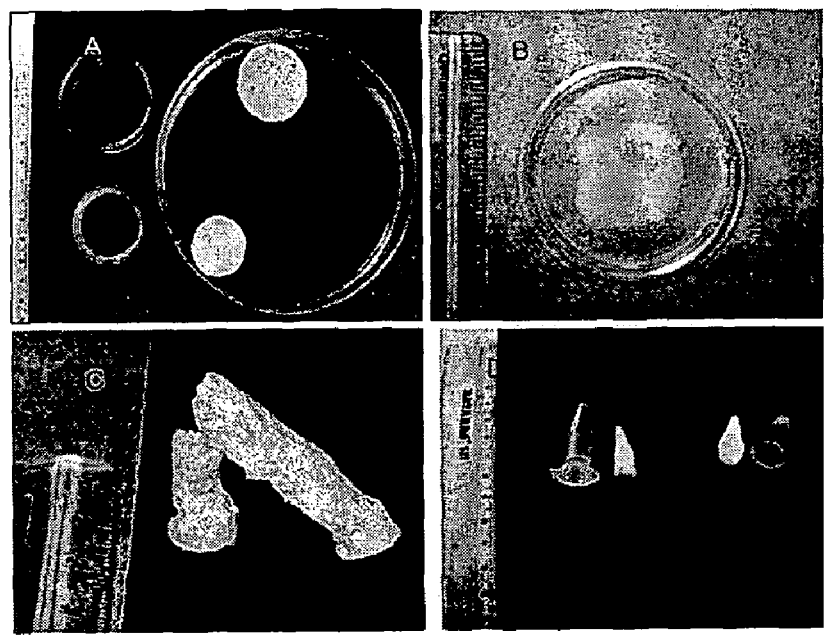

(E and F) Transmission electron microscopy (TEM) showing surfactant mediated fusion of PDLLA-CTAB nanoparticles FIG. 2 shows fabrication of polymeric membranes and three dimensional structures using surfactant mediated fusion of PDLLA-CTAB particles (A) Polymeric membranes of different sizes formed after the fusion of PDLLA-CTAB particles in presence of ethanol at room temperature (B) Polymeric membrane of square dimension fabricated using fusion process (C) PDLLA-CTAB particles were filled in cylindrical moulds (falcon plastic tubes) and wetted with ethanol to obtain the three dimensional structures (D) Particle fused using eppendorf tube as a mould resulting in three D structure.

Figure 3:
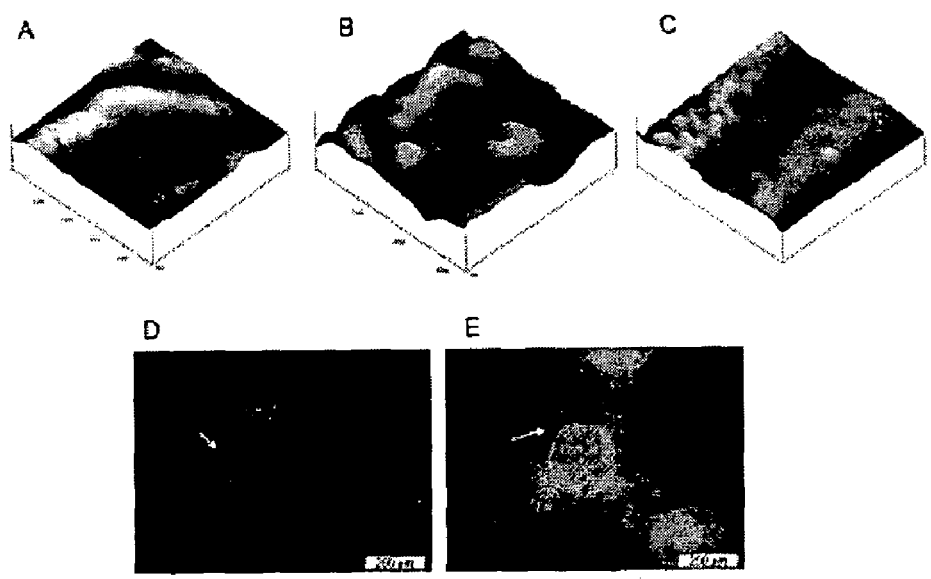

FIG. 3 shows microscopy images of surfactant removal and fusion region formation. (A, B and C) Atomic force microscopy (AFM) images of the surface of PDLLA-CTAB particles before and after fusion (A) The adsorption of surfactant molecules on the surface of particles can be seen before the process of fusion (B) After the surfactant mediated fusion of particles in presence of ethanol, polylactide surface with pores can be seen due to removal of the adsorbed surfactant molecules (C) The same particle at lower magnification of the surface showing multiple pores (D and E) Formation of polymeric bridges between fluorescent PDLLA-CTAB particles after the process of surfactant mediated fusion in ethanol. Fine fluorescent bridges can be seen between the particles lying nearby as indicated by the arrows.

Figure 4:
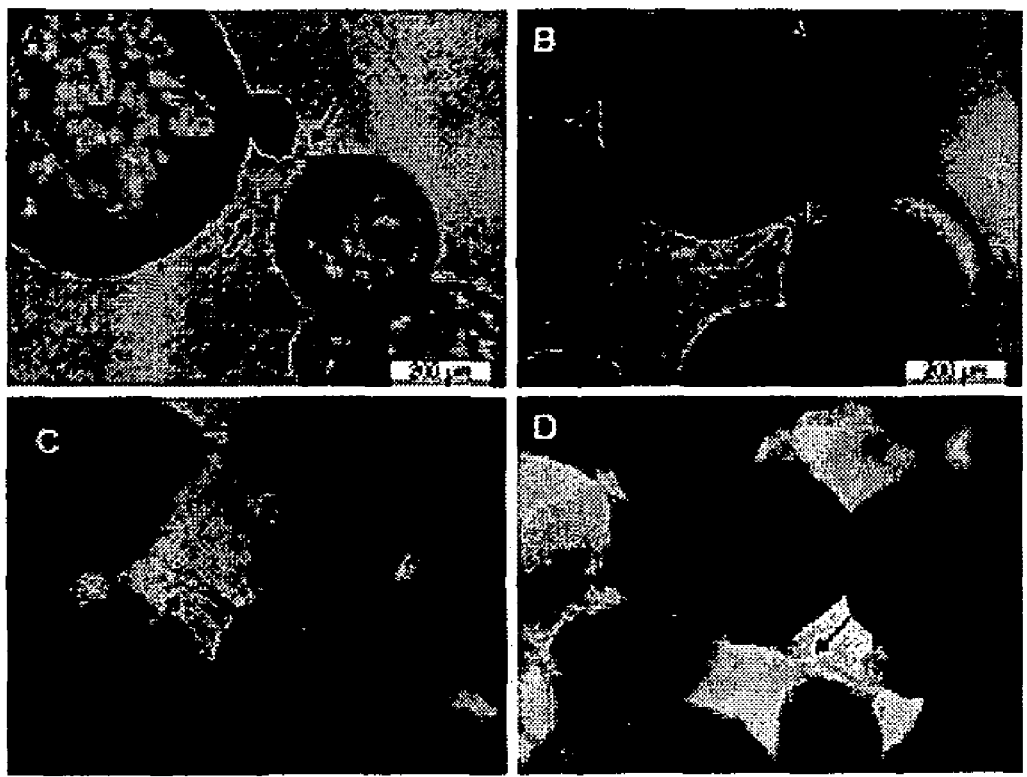

FIG. 4 shows fusion of PDLLA-CTAB and PLGA-CTAB particles in presence of ethanol and methanol (A, B) polymer bridges formed between PDLLA-CTAB particles in presence of ethanol as indicated by the arrows (C D) polymer bridges formed between PDLLA-CTAB particles in presence of methanol. The polymer bridges are more prominent in this case as the process of fusion in methanol is much stronger as compared with ethanol.

Figure 5:
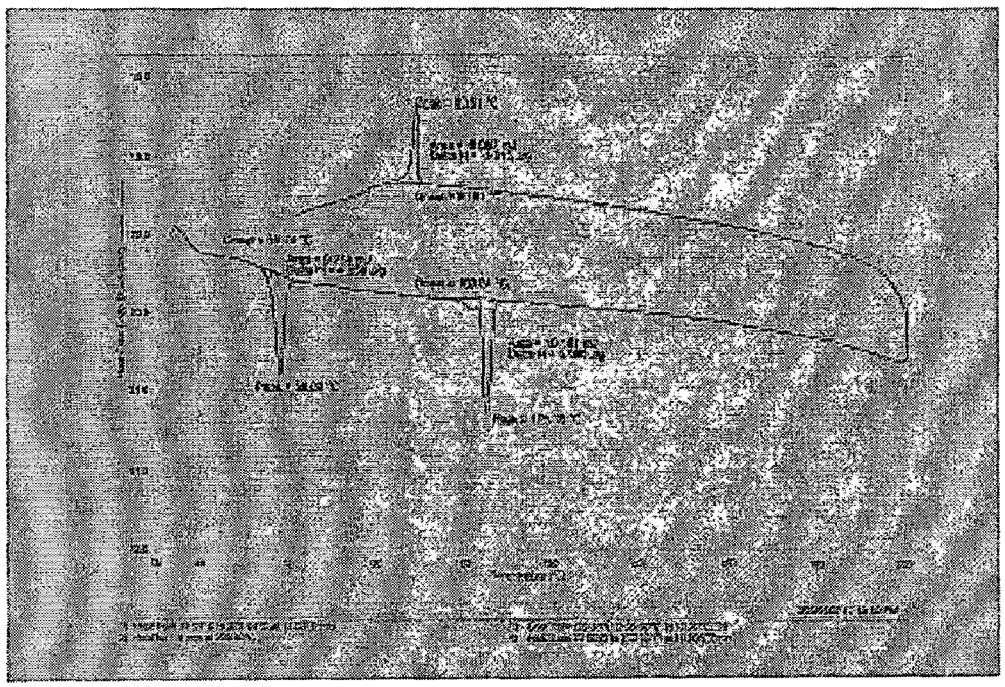
Figure 5:
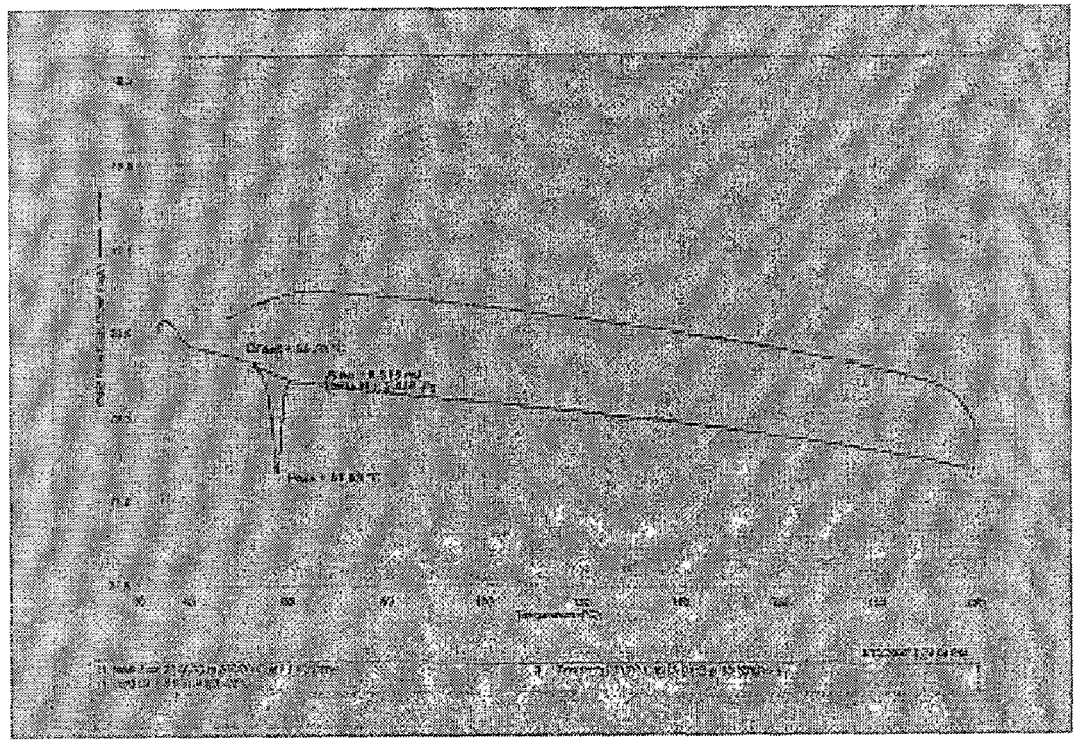

FIG. 5 shows differential scanning calorimetry (DSC) of PDLLA-CTAB particles (A) DSC of PDLLA-CTAB particles before the process of fusion. The glass transition temperature is around 58° C. The other two peaks are of the excipients used during particle preparation (B) DSC of PDLLA-CTAB scaffold after the process of fusion of the particles which shows no change in the glass transition temperature of the polymer. Since the particles are highly porous most of the encapsulated excipients are washed during ethanol treatment, thus the other two peaks are missing.

Figure 6:
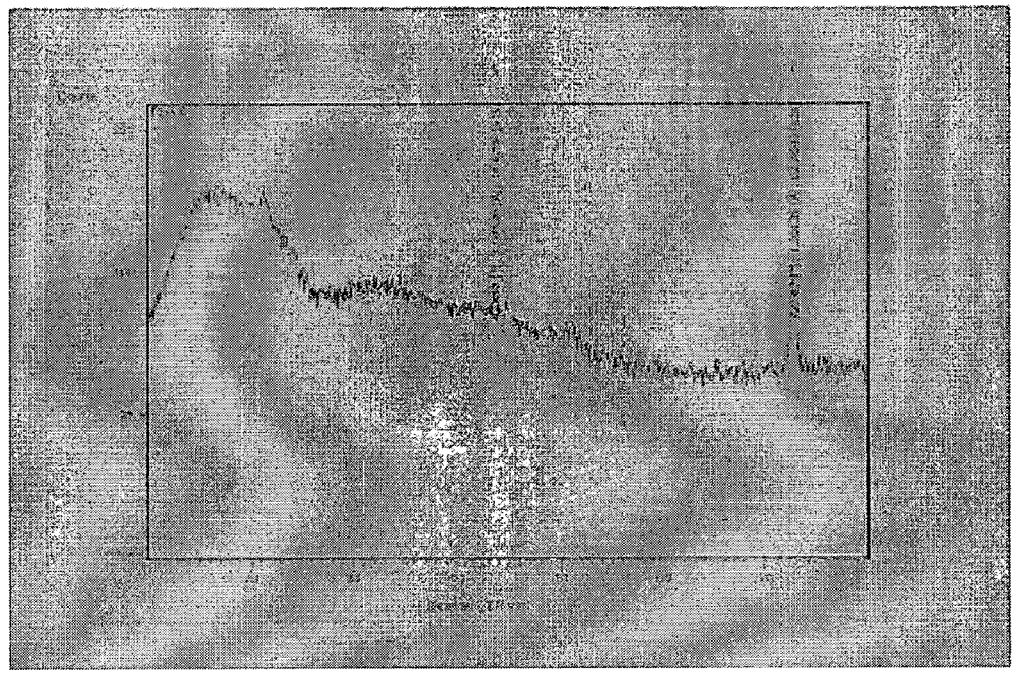
Figure 6:
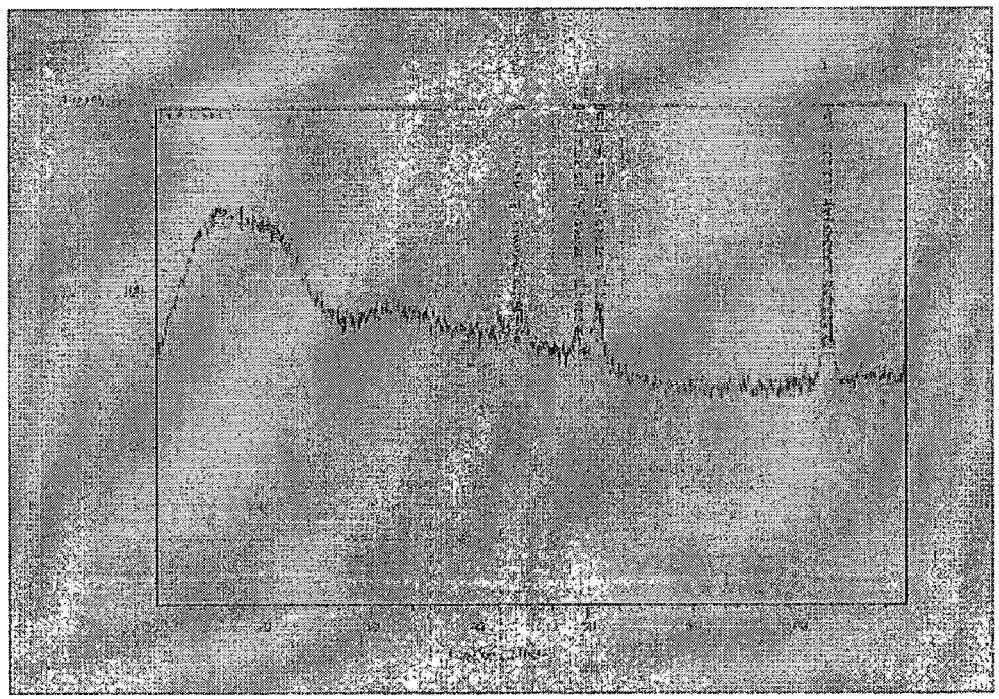

FIG. 6 shows X-ray powder diffraction of PDLLA-CTAB particles before and after ethanol treatment (A) Diffraction pattern (from 0° to 30°) showed characteristic amorphous nature of PDLLA polymer (B) There was no change in the amorphous nature after the process of fusion of PDLLA-CTAB particles.

Figure 7:
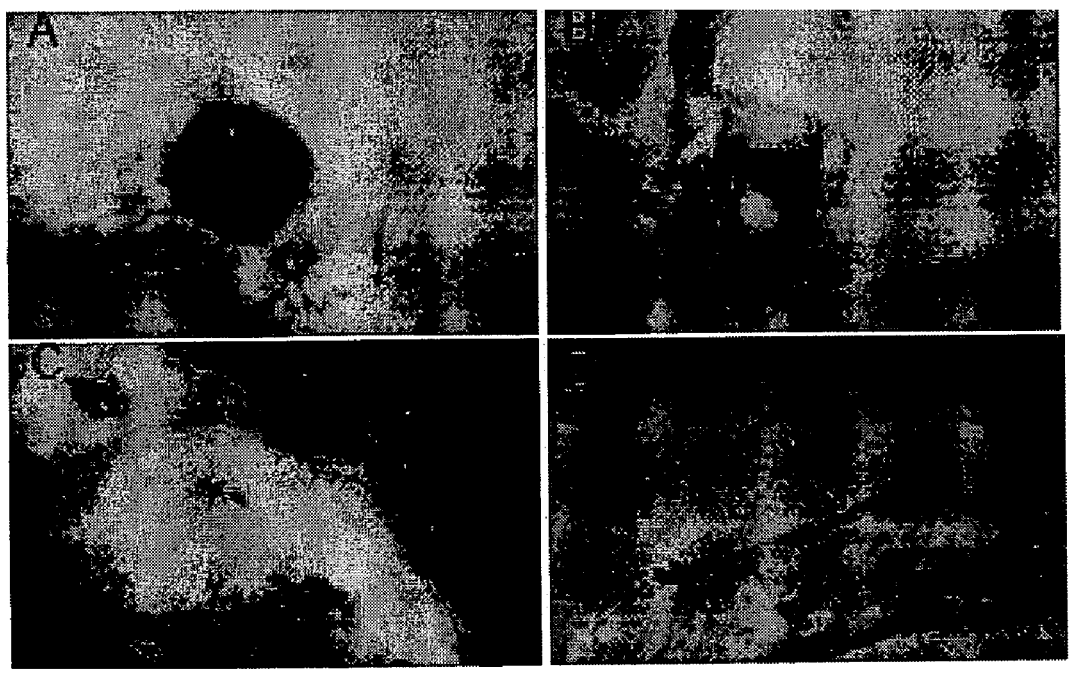

FIG. 7 shows evaluation of polylactide polymeric membrane formed by fusion process for wound healing (A) 2×3 cm uninfected open wound, day 5

(B) Open wound treated with the polymer membrane, day 5

(C, D) Rats after 21 days of treatment. (C) Rat with open wound. (D) Rat treated with polymeric membrane, the wound closure was better in the group treated with the polymeric membrane.

DETAILED DESCRIPTION OF THE INVENTION

The present invention provides a room temperature process for the fabrication of biodegradable polymer scaffold useful for tissue engineering, therapeutic compound delivery and/or wound dressing. The scaffold disclosed in the present invention comprises biodegradable polymer and the higher order structure fabrication take place in presence of surfactant, and alcohol. The present invention further provides a process for the biodegradable polymer scaffold encapsulating growth factors, proteins and/or peptides and or drugs of choice.

The present invention particularly provides self-assembly of polylactide polymer particles to scaffolds of the desired size, shape and topology at room temperature suitable for different bio-medical applications particularly for regenerative medicine.

No report exists till today on surfactant mediated self assembly of biodegradable polymers in to higher order structure. As these polymer particles are biodegradable and can be made porous their self assembly provides an ideal method for the fabrication of scaffold having desired pore size, biodegradability and functionality which are the most essential requirements of scaffold design.

In the present invention a novel method of PDLLA scaffold fabrication has been described wherein surfactant molecules mediate the fusion and self-assembly of polylactide particles in a controlled manner at room temperature into membrane types structures. Polylactide composite membrane is currently used as skin substitute (Suprathel®, www.suprathel.com) for treatment of burn victims (Uhlig C et al. Suprathel—An innovative, resorbable skin substitute for the treatment of burn victims. Burns 2007; 33: 221-29) but has the limitation of not supporting dermal growth or entrapping bioactive growth factors. Polylactide membrane prepared by the surfactant mediated fusion process described in the present invention was tested as an artificial skin substitute for wound healing. The mechanism involved in such surfactant mediated fusion of polylactide particles into membrane type structure at room temperature was investigated. The results suggest that desorption of surfactant molecules from the surface of particles in presence of ethanol created regions where the polymer solubility increases transiently and results in fusion into higher order structures. The surfactant mediated particle fusion process disclosed in the present invention provides a better alternative to fabricate higher order polymeric structures for various bio-medical applications.

In one embodiment, a biodegradable polymer refers to a material, which is degraded in the biological environment of the cell or subject in which it is found.

The biodegradable polymer can be natural biodegradable polymer, modified natural biodegradable polymer, synthetic biodegradable polymer or combinations thereof.

The term "PLGA" as used herein is intended to refer to a polymer of lactic acid alone, a polymer of glycolic acid alone, a mixture of such polymers, a copolymer of glycolic acid and lactic acid, a mixture of such copolymers, or a mixture of such polymers and copolymers. Preferably, the biodegradable polymer will be poly lactide-co-glycolide (PLGA).

Unless otherwise noted, the term microparticles can be used to encompass microparticles, microspheres, and microcapsules. Active agents to be incorporated into the microparticles are synthetic or natural compounds which demonstrate a biological effect when introduced into a living creature. Contemplated active agents include peptides, small molecules, carbohydrates, nucleic acids, lipids, and proteins. Proteins contemplated for use include potent cytokines, including various hematopoietic factors such as G-CSF, GM-CSF, M-CSF, MGDF, the interferons (alpha, beta, and gamma), interferon consensus, the interleukins (1-12), erythropoietin (EPO), fibroblast growth factor, TNF, TNFbp, IL-1ra, stem cell factor, nerve growth factor, GDNF, BDNF, NT3, platelet-derived growth factor, and tumor growth factor (alpha, beta), osteoprotegerin (OPG), and OB protein.

Biodegradable polymers are well known within the art as carriers for biologically active materials. Such biologically active materials may include therapeutic agents such as drugs, antibiotics, enzymes, and hormones. Further, polymers which form hydrogels can be used as carriers for cell suspensions and to increase the functional life of a carried material or agent.

Other useful biodegradable polymers or polymer classes include the following: polydioxanones, polycarbonates, polyoxalates, poly(.alpha.-esters), polyanhydrides, polyacetates, polycaprolactones, poly(orthoesters), polyamino acids, polyamides and mixtures and copolymers thereof.

Additional useful biodegradable polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of .alpha.-amino acids, copolymers of .alpha.-amino acids and caproic acid, copolymers of .alpha.-benzyl glutamate and polyethylene glycol, copolymers of succinate and poly(glycols), polyphosphazene, polyhydroxy-alkanoates and mixtures thereof. Binary and ternary systems are contemplated.

The process disclosed in the present invention is useful for preparation of stable structures of desired size and shape such as the polymer membranes and scaffolds for tissue engineering, drug delivery and/or wound dressing.

The present invention provides a biodegradable polymer scaffold made from fusion of polymer particles entrapping protein/drugs/growth factors.

The present invention provides a process for fabrication of higher order structure using polymer particles which are made using solvent evaporation method or spray drying. Both nanoparticles and microparticles of different sizes could be used to fuse in to higher order structure.

The present invention provides a process for preparation of biodegradable polymer scaffold, wherein the polymer particles used are polylactide particles.

The present invention relates to the biodegradable polymer particles wherein the particles are prepared by encapsulating the polymer particles by components such as growth factors/drugs and proteins in the particles. The encapsulated particles are treated with surfactants such as cetyl trimethyl ammonium bromide (CTAB), SDS or Tween 20.

In accordance with the present invention, there is provided a process of preparation of a biodegradable polymer scaffold useful for tissue engineering, therapeutic compound delivery and/or wound dressing, wherein the process comprises spreading surfactant coated polymer particles on a support;

soaking the particles with alcohol; and washing the above with water to obtain the polymer scaffold.

In one embodiment, there is provided a process of preparation of a biodegradable polymer scaffold, wherein the process comprises spreading cetyl trimethyl ammonium bromide (CTAB) coated polymer particles of Poly-DL-lactide (PDLLA) on a support; soaking the particles with ethanol or methanol; and washing the above with water to obtain the polymer scaffold.

In another embodiment, there is provided a process of preparation of a biodegradable polymer scaffold, wherein the process comprises spreading cetyl trimethyl ammonium bromide (CTAB) coated polymer particles of Poly lactide co-glycolide particle on a support; soaking the particles with ethanol or methanol; and washing the above with water to obtain the polymer scaffold.

The process of preparation of the biodegradable polymer scaffold disclosed in the present invention optionally comprises encapsulating the surfactant coated polymer particles with growth factors, protein or therapeutic compound.

In one embodiment, there is provided a solid support for the process of preparation of the biodegradable polymer scaffold disclosed in the present invention.

The process of preparation of the scaffold as disclosed in the present invention, wherein different design of mould can be used to make polymeric structure of different sizes and shapes of said polymer scaffold.

One embodiment of the present invention provides the biodegradable polymer such as Poly-DL-lactide (PDLLA), polylactide-co-glycolide (PLGA), aliphatic polyesters, poly (amino acids), copoly(ether-esters), polyalkylene oxalates, polyamides, poly(iminocarbonates), polyorthoesters, polyoxaesters, polyamidoesters, poly(anhydrides), polyphosphazenes and biopolymers, poly(amino acids), poly(anhydrides), poly(orthoesters), poly(phosphoesters), polylactones, poly(sebacate), poly(hydroxy acids), copolymers thereof, single polymer, copolymer, terpolymer, or polymer blend, and is selected from the group consisting of polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, and modified proteins; and combination thereof.

Another embodiment of the present invention provides the surfactant such as cationic, anionic and neutral surfactant for coating the polymer particles. The examples of surfactant are cetyl trimethyl ammonium bromide (CTAB), sodium dodecyl sulphate (SDS), Tween 20.

Still another embodiment of the present invention provides alcohol selected from a group consisting of ethanol, methanol and propanol for preparation of the biodegradable polymer membrane scaffold.

In one embodiment the process of preparation of the scaffold as disclosed in the present invention uses ethanol.

In another embodiment the process of preparation of the scaffold as disclosed in the present invention uses methanol.

In yet another embodiment, the present invention provides the growth factor selected from a group consisting of TGF-.beta. family, bone morphogenic proteins, fibroblast growth factors-1 and -2, platelet-derived growth factor-AA, and -BB, platelet rich plasma, vascular endothelial cell-derived growth factor and epidermal growth factor (EGF), platelet derived growth factor (PDGF), insulin-like growth factor (IGF), basic fibroblast growth factor (bFGF), bone morphogenic proteins (BMPs) and combinations thereof.

One of the preferred embodiments of the present invention provides a biodegradable polymer scaffold useful for tissue engineering, therapeutic compound delivery and/or wound dressing, wherein said scaffold is obtained by the process as disclosed in the present invention.

In another embodiment, the present invention provides the biodegradable polymer scaffold for tissue engineering, wherein tissue engineering comprises culturing cells selected from a group consisting of stem cells, embryonic stem cells, pluripotent cells, multipotent cells, chondrocytes, osteoblasts, osteocytes, fibroblasts, bone marrow cells, stromal cells, chondrocyte progenitors, osteoclasts, endothelial cells, macrophages, adipocytes, monocytes, plasma cells, mast cells, umbilical cord cells, leukocytes, epithelial cells, myoblasts, and precursor cells derived from adipose tissue.

In another embodiment, the present invention provides the biodegradable polymer scaffold useful for delivery of therapeutic compound such as a peptide, protein, nucleic acid or a drug.

In one embodiment, the present invention provides use of the biodegradable polymer scaffold disclosed in the present invention for in vitro three dimensional growth of animal cells.

In another embodiment, the present invention provides use of the biodegradable polymer scaffold disclosed in the present invention for controlled drug delivery device.

In yet another embodiment, the present invention provides use of the biodegradable polymer scaffold disclosed in the present invention for tissue engineering of artificial skin.

In still yet another embodiment, the present invention provides use of the biodegradable polymer scaffold disclosed in the present invention for wound healing and skin grafting.

The present invention provides a process for preparation of biodegradable polymer scaffold by transferring the newly formed membrane of the fused polymer particles to water, wherein the fused polymer particles become rigid and can be handled with ease.

The present invention provides a process for preparation of biodegradable polymer scaffold, wherein the fusion of the polymer particles occurs at the contact points between the particles retaining the morphology and structure of the particles. The fusion of the particle occurs when the surfactant coated polymer particles at subjected to alcohol such as ethanol. This phenomenon of fusion of the polymer particles results from surfactant mediated fusion of polymer particles which is associated with sudden desorption and collective motion of the surfactant molecules during alcohol treatment. The fusion of the polymer particles occurs at room temperature or at much lower temperature.

The present invention provides a process for preparation of biodegradable polymer scaffold, where the collective motion of the surfactant molecules creates a transient local environment which is entropically favorable for the surface of the polymer particles to achieve a partly solubilized or molten state when it comes in contact with ethanol.

The present invention provides a process for preparation of biodegradable polymer scaffold where the surfactant used for coating the polymer particles comprises of SDS and Tween 20 to mediate fusion of polymer particles.

The present invention provides a process for preparation of biodegradable polymer scaffold from polymer particles where the membrane has stable higher order structure.

The present invention provides a biodegradable polymer membrane/scaffold wherein the components such as drugs/growth factor/proteins are entrapped in the polymer particles.

The present invention provides a biodegradable polymer scaffold wherein the polymer membrane is used in vitro three dimensional growth of animal cells.

The present invention provides a biodegradable polymer scaffold wherein the polymer membrane is used as controlled drug delivery device.

The present invention provides a biodegradable polymer scaffold wherein the polymer membrane is used for tissue engineering of artificial skin.

The present invention provides a biodegradable polymer scaffold wherein the polymer membrane is used for wound healing and skin grafting.

The present invention provides a biodegradable polymer scaffold wherein the polymer scaffold is used in various biomedical applications such as tissue engineering, controlled drug delivery implants and as artificial skin for burn treatment.

The present invention provides a biodegradable polymer scaffold that forms a stable particle network or scaffold.

The present invention provides a biodegradable polymer scaffolds formed by surfactant mediated fusion of polymer particles such as Poly-DL-lactide (PDLLA) and polylactide-co-glycolide (PLGA). The polymer scaffold is used in various biomedical applications.

The present invention provides the biodegradable polymer scaffold where encapsulated biodegradable polymer particles used are encapsulated with components such as drugs that can be easily stored and fused into scaffolds.

The present invention provides a process for preparation of biodegradable polymer scaffold by surfactant mediated fusion of polymer particles, wherein the surfactants such as cetyl trimethyl ammonium bromide (CTAB), SDS and Tween 20 is used.

The present invention provides a process for preparation of biodegradable polymer scaffold wherein fusion of polymer particles of the desired size takes place in a controlled and gentle manner that leads to the formation of a stable three dimensional structure of the desired shape and size by packing the polymer particles in a mold and wetting with ethanol.

The present invention provides a process for preparation of biodegradable polymer scaffolds at room temperature without changing the bulk properties of the polymer.

The present invention provides a process for preparation of biodegradable polymer scaffolds wherein the membrane of the scaffold is encapsulated by components such as proteins, drugs or growth factors. The preparation of the biodegradable polymer membrane scaffolds does not alter the properties of the polymer particles.

The present invention provides a process for preparation of biodegradable polymer scaffolds wherein the surfactant such as CTAB molecules are desorbed during the fusion reaction when the surfactant coated polymer surface comes in contact with ethanol.

The present invention also provides surfactant free biodegradable polylactide scaffolds.

The present invention provides a process for preparation of biodegradable polymer scaffolds by fusion of CTAB coated polylactide-co-glycolide polymer particles by methanol treatment.

The present invention provides a process for preparation of biodegradable polymer scaffolds by wetting the polymer particles with ethanol to fuse and sterilizes them effectively.

The present invention provides a bioactive three dimensional scaffold support that can be used in cell growth and differentiation, at the same time releasing various growth factors into the tissue microenvironment. The polymer particles that are fused to form the scaffold are first formulated by encapsulating various components such as proteins drugs or growth factors.

In the present invention, a process is described where the sudden desorption of the surfactant molecules during alcohol treatment creates a transient local environment were the surface of the polymer achieves a partly solubilized or molten state, so that as the particles come in contact in the evaporating alcohol phase, they form fusion regions. The process terminates almost immediately as the CTAB surfactant molecules get dispersed into the alcohol phase. This ensures that the fusion occurs at the points of contact between the particles and the particle morphology is maintained. The ease of the process and its occurrence at ambient temperature makes this method of surfactant mediated fusion of biodegradable particles attractive for various biomedical applications such as tissue engineering, controlled drug delivery implants and artificial wound dressings for burns.

Surprisingly it was found that the properties of the polymer such as the molecular weight, glass transition temperature, viscosity are not altered during the preparation of the three dimensional structures of the biodegradable polymer.

Formulation and Characterization of Polymer Particles

Figure 1:
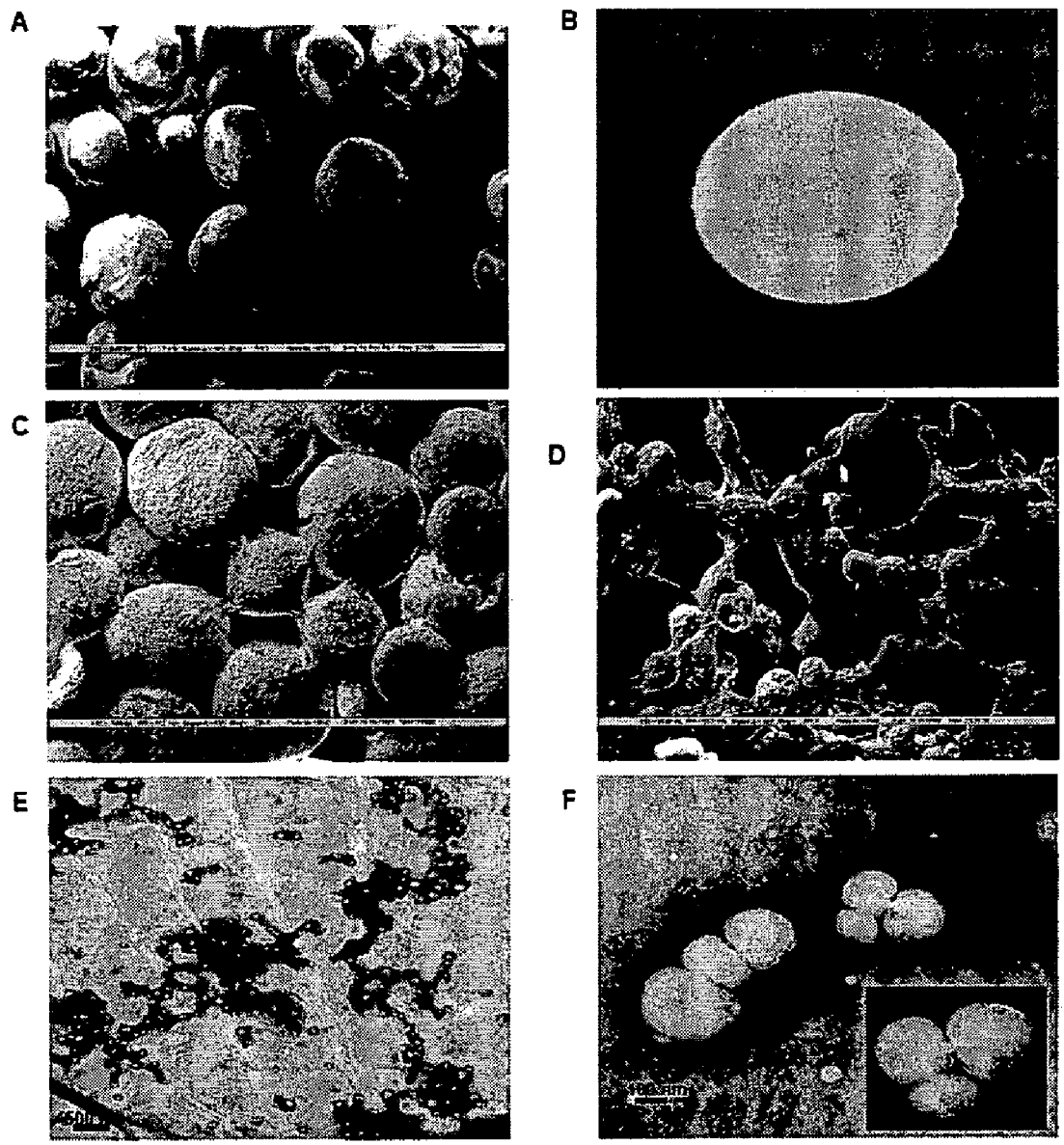
FIG. 1 shows microscopy of polymer particles and its fusion process.

Polylactide particles of different sizes were prepared using solvent evaporation method (Kanchan V, Panda A K. Interactions of antigen loaded polylactide particles with macrophages and their correlation with immune response. Biomaterials 2007; 28: 5344-57). The PDLLA-CTAB macro particles were made porous by incorporating sucrose both in internal and external aqueous phases during the particle formulation (Sahoo S K, Panda A K, Labhasetwar V. Characterization of porous PLGA/PLA microparticles as a scaffold for three dimensional growth of breast cancer cells. Biomacromolecules 2005; 6: 1132-39). Surfactant coating was achieved by incorporation of CTAB in the external aqueous phase during the secondary emulsion step of solvent evaporation method. The CTAB coated PDLLA macro particles (PDLLA-CTAB) were free flowing, porous and had an average size of 300 µm as measured by the particle size analyzer (FIG. 1 A). Particles made from different polymers such as PLLA, PLGA with PVA and other surfactants in the surface have similar morphology and size range as observed for PDLLA polymer. Both PDLLA-CTAB and PDLLA-PVA macro particles showed a spherical morphology. The PDLLA-CTAB micro particles had an average size of 2-4 µm and the PDLLA-CTAB nano particles had an average size of 200-400 nm.

Fusion of Polymer Particles in to Membrane Like Structures

Fusion of PDLLA-CTAB macro particles was observed in presence of ethanol at room temperature. Addition of ethanol to evenly spread PDLLA-CTAB particles on petri dishes formed a stable network of particles resulting in the formation of a membrane (FIG. 1 B). The polymeric membrane at this stage was very plastic in nature and stabilized in a few minutes in presence of ethanol. Removal of ethanol and washing with sterile water resulted in stable polymeric membrane like structures (FIG. 1 B). Polymeric membranes of desired size and thickness can be fabricated using the above fusion process. The fusion regions between the particles were observed using the scanning electron microscope (FIG. 1 C, D). These essentially consist of polymeric protrusions attaching each other forming a stable network structure (FIG. 1 D). CTAB coated PDLLA nanoparticles also fused as efficiently as the surfactant coated macro particles (FIG. 1 E-F). Fusion of PDLLA-CTAB nanoparticles was also associated with surface attachment of particle with each other (FIG. 1 F). By spreading the polymer particle in different sized petri dishes and wetting with ethanol, different sized membranes were fabricated at room temperature (FIG. 2 A). 10 mg of PDLLA-CTAB particles upon fusion yielded around 2 cm$^2$ polylactide membrane (FIG. 2 A, B). Square type membrane and large size scaffold could also be fabricated from these particles using appropriate mould (FIG. 2 B). For the fabrication of three dimensional structures, the PDLLA-CTAB particles were filled in moulds such as normal eppendorf tube and 25 ml falcon tube and wetted with ethanol followed by washing with water. This resulted in fabrication of scaffolds of desired size having stable structure (FIG. 2 C, D). Thus apart from forming membrane type structure, the process can be used to fabricate scaffold of different design and shapes.

PDLLA-CTAB particles when wetted with water did not fuse to form higher order structures at room temperature and remain as dispersion. PDLLA particles coated with PVA (PDLLA-PVA) also did not fuse and maintained their discreteness in both water and ethanol. When PDLLA pellets without any surfactant molecules were wetted with DCM, ethanol and water respectively, PDLLA pellets got solubilized in DCM, but did not fuse immediately in presence of ethanol and water. Wetting of PDLLA polymer crystals in presence of both CTAB and ethanol did not result in fusion of polymer. Fusion in to membrane type structure in presence of ethanol at room temperature only took place using particles that were coated with surfactant. This indicated that the presence of surfactant molecules on the surface of the polymer particles play an important role in the fusion of particles into higher order structure.

Desorption of Surfactant Molecules During Ethanol Treatment from the Particles

As only surfactant coated polymer particles fused in the presence of ethanol, it was of interest to know the role of surfactant in such fusion process. Presence of CTAB on the polymer particle surface during ethanol treatment was quantitated by measuring the surface charges of the particle. Zeta potential measurement of PDLLA-CTAB micro particles before and after ethanol treatment indicated that CTAB molecules were desorbed from the surface of the particles during ethanol treatment. Different batches of polylactide particles were prepared with 1%, 0.1%, 0.03%, 0.016%, 0.008%, and 0.0016% CTAB in external aqueous phase (EAP). Particles with 1% CTAB showed a positive zeta potential of +45±10 mV, which decreased while using lower concentrations of CTAB during particle formulation. Particles with 0.016% CTAB had a positive zeta potential value of +16±5 mV, where as particles with 0.008% and 0.0016% CTAB showed a negative zeta potential value of −0.5 and −20.8 mV respectively. This decrease in positive zeta potential value and the shift towards negative values indicated a decrease in the amounts of positively charged CTAB molecules on the surface of the polylactide particles. After ethanol treatment, the 1% PDLLA-CTAB scaffold was broken down into smaller fragments and the zeta potential measured. These fragments showed a negative zeta potential value of −20.7 mV, which indicated desorption of CTAB molecules from the particles during ethanol treatment. Overnight treatment of the PDLLA-CTAB particles in MQ water did not change the zeta potential of the particles, indicating that the surfactant molecules are stably adsorbed on the particle surface. Atomic Force Microscopy (AFM) studies of the surface of 1% PDLLA-CTAB particles, both before and after ethanol treatment, showed that CTAB molecules are removed from the particle surface during ethanol treatment (FIGS. 3, A, B and C). The surface of the particle looked smooth with CTAB coating before ethanol treatment (FIG. 3 A) where as it looked porous after ethanol treatment (FIG. 3 B, C) indicating desorption of the molecule from the surface leaving behind pores. Polylactide particles prepared with 1%, 0.1%, 0.03%, and 0.016% CTAB fused when wetted with ethanol, where as particles prepared with 0.008% and 0.0016% CTAB did not fuse, indicating that the adsorbed surfactant molecules were not sufficient enough to mediate the process of fusion in the latter two cases. It was observed that the process of fusion was immediately initiated on wetting with ethanol and after the process of fusion, further fusion between two such scaffolds did not occur in presence of ethanol. This indicated that desorption of surfactant molecules from the surface of the particles during ethanol treatment played an important part in particle fusion and the process gets terminated when surfactant molecules are completely removed by solvent.

Polylactide particles prepared using SDS/Tween 20 in the external aqueous phase also fused into higher order structures in presence of ethanol. In case of SDS coated PDLLA particles, colorimetric estimation of SDS showed that substantial amounts were desorbed from the particle surface during ethanol treatment. Desorption of SDS from polymer particles was not significant in presence of water (Table 1). PDLLA-PVA particles did not fuse in presence of ethanol and colorimetric estimation of PVA, both before and after ethanol treatment, showed that PVA is stably adsorbed on PDLLA-PVA particles during ethanol treatment (Table 1). These observations suggested that the surfactant mediated fusion of polylactide particles in ethanol was associated with desorption of surfactant molecules in ethanol and was independent of the charge and nature of the surfactant.

Visualization of Fusion Regions Using Fluorescent Polymer Particles

Fusion process was visualized by using fluorescent PDLLA-CTAB particles prepared by incorporating coumarin dye in the organic phase during particle formulation. These fluorescent polymer particles containing CTAB on the surface also fused in similar manner as described above to form membrane like structure. Fusion regions were mostly formed at the points of contact between the polymer particles. In addition to fusion regions formed at the points of contact between the particles, fine fluorescent polymer bridges between PDLLA-CTAB particles could be detected during the fusion in presence of ethanol (FIG. 3 C, D). These fine bridges may be indicative of the transient regions formed by the desorbed surfactant molecules between particles, through which the polymer has solubilized and formed connection bridges between particles. The process of membrane formation was not due to aggregation of particles but was through fusion of particle during ethanol treatment. Wetting plain PDLLA pellets and PDLLA-PVA particles with ethanol containing 1% CTAB or even after vortexing did not result in fusion of the polymer. This inferred that the mode of action of the surfactant molecules in the rapid fusion of PDLLA-CTAB particles in ethanol is different from its usual way of solubilization of sparingly soluble substances in solvents through formation of micelles.

Fusion of Different Polymer Particles Using Other Alcohols

To further evaluate whether CTAB molecules can mediate the fusion of other related polymers in ethanol, particles of poly L-lactide (PLLA), poly D, L-lactide-co-glycolide (PLGA) and polystyrene (PS) were prepared with 1% CTAB in external aqueous phase. No fusion of particles was observed with PLLA-CTAB, PLGA-CTAB and PS-CTAB particles in presence of ethanol despite CTAB desorption from the surface of particles in all cases. However in presence of methanol, both PDLLA-CTAB and PLGA-CTAB particles fused well. It was observed that the process of fusion was much stronger with methanol with formation of more prominent fusion regions as compared with ethanol (FIG. 4 A-D). In case of ethanol, the connecting bridges were thin (FIG. 4 A-B) where as in case of methanol, the connecting bridges covered a large surface area of the polymer particles (FIG. 4 C-D). PLLA-CTAB and PS-CTAB particles did not fuse in presence of these solvents. To assess the solubility profile of the above polymers in ethanol and methanol, equal amounts of PDLLA, PLGA, PLLA and PS pellets were taken and kept in 50 ml of ethanol and methanol and observed overnight. There was no immediate fusion of any of the pellets in ethanol and methanol. After overnight treatment, it was observed that the PDLLA pellets stuck to each other in ethanol, and almost fused to one mass in methanol. In case of PLGA, there was hardly any sticking of the pellets in ethanol, but with methanol the pellets stuck to each other. PLLA and PS pellets did not fuse and maintained their discreteness both in ethanol and methanol even after overnight treatment. The comparative solubility profile of the polymers in ethanol and methanol correlated well with the process of fusion of these polymer particles. The solubility of PDLLA is higher in methanol as compared to ethanol, and the process of fusion of PDLLA-CTAB particles in presence of methanol was more rapid and stronger than with ethanol. In the case of PLGA, its solubility in ethanol was poor as compared with PDLLA, but showed better solubility in methanol. PLGA-CTAB particles fused well with methanol, but not with ethanol. PLLA and PS have poor solubility in methanol and ethanol and PLLA-CTAB and PS-CTAB particles did not fuse in presence of either of the solvents. The process of fusion in PDLLA-CTAB particles with ethanol and methanol was inhibited by adding PLLA to PDLLA in the ratio of 40:60 respectively during particle formulation. These observations suggested that apart from the desorption of surfactant molecules from the surface of the particles by alcohol, solubility profile of the polymer in the alcohol/surfactant mixture play an important role in fusion of polymer particles in to higher order structure.

Effect of Temperature in the Surfactant Mediated Fusion of Polymer Particles

Temperature play an important role in fusion of polylactide particles, since raising the temperature above the glass transition temperature (Tg) of PDLLA of about 60° C. can result in fusion of PDLLA material or particles. Residual water present in the polylactide particles prepared by double emulsion solvent evaporation method has been reported to lower the Tg of the polylactide particles (Passerini N, Craig D Q M. An invention into the effects of residual water on the glass transition temperature of polylactide microspheres using modulated temperature DSC. Journal of Controlled Release 2001; 73: 111-5). Differential scanning calorimetric studies of PDLLA-CTAB particles showed that the glass transition temperature was not much lowered during the formulation of the particles. The particles showed a Tg of 58° C. which is not much less than that of the raw polymer (FIG. 5 A). Calorimetric studies also showed that there was no change in the polymer characteristics after the fusion of particles into higher order structures (FIG. 5 B). To further check the stability of the PDLLA-CTAB particles, one batch of dry particles were kept at 37° C. in an incubator overnight and another batch of particles were wetted with water at 37° C. In both the cases, the particles were stable and no fusion took place. To evaluate the effect of temperature during wetting with ethanol, PDLLA-CTAB particles were wetted with chilled ethanol at different temperatures and fusion of PDLLA-CTAB particles was observed in presence of ethanol even at −20° C. These observations suggested that the desorbing surfactant molecules played a critical role in forming the fusion regions between polylactide particles in ethanol and was independent of temperature and the effect of the solvent in mediating the process of fusion. X ray diffraction study of the polymer particles and the scaffold showed similar amorphous nature of the polymer, indicating that the fusion mediated by the surfactant molecules did not change the intrinsic property of the polymer particles (FIG. 6 A, B).

Evaluation of Polymeric Membrane as Artificial Skin Substitute

Polylactide membrane formulated by the above fusion process was evaluated as artificial skin substitute for wound healing in experimental animal models. Ethanol treatment not only removed the surfactant molecules from the particles while making the membrane but also sterilized the membranes for medical application. The membrane (FIG. 1 B) was directly transferred onto the non infected full thickness wounds of Wistar rats. Wound scoring was done in the group of animals treated with the polymeric membrane and compared with those animals which did not receive any treatment with the membrane. Preliminary evaluation of the polymeric membrane showed good results. The polymeric membrane composed of the fused polylactide particles adhered to the wound bed and did not cause adverse reactions during the entire closure of the wound (FIG. 7 A-D). The porous nature of the polymeric membrane maintained a moist environment needed for proper wound healing, at the same time preventing excessive loss of fluids. It also serves as a temporary artificial skin substitute till complete healing and regeneration of the wound takes place. In the collagen assay it was found that wound treated with polylactide membrane has more collagen content in the skin as compared to the control. The collagen content in healed skin of the animals treated with polylactide membrane was around 30 μg/ml in comparison to 14 μg/ml of collagen in the skin of the untreated animals.

Having generally described the invention, the same will be more readily understood through reference to the following examples which are provided by way of illustration, and are not intended to be limiting of the present invention, unless specified.

EXAMPLES

It should be understood that the following examples described herein are for illustrative purposes only and that various modifications or changes in light of the specification will be suggestive to person skilled in the art and are to be included within, the spirit and purview of this application and the scope of the appended claims.

Example 1

Materials

PDLLA (45 kDa), and PLGA (45 kDa) were purchased from Durect Corporation (Pelham, USA). The surfactants Cetyltrimethyl ammonium bromide (CTAB), Sodiumdodecyl Sulphate (SDS) and Tween 20 were procured from Amresco chemicals, USA. Polyvinyl alcohol (PVA) and polystyrene were from Sigma Chemicals, USA. 6-Coumarin (8037L) was from Polysciences, Warrington, Pa. Sircol collagen assay kit was from Biocolor life science assays, UK.

Preparation of Surfactant Coated Polymer Particles

PDLLA particles were prepared using w/o/w double emulsion solvent evaporation method (Katare Y K, Muthukumaran T, Panda A K. Influence of particle size, antigen load, dose and additional adjuvant on the immune response from antigen loaded PLA microparticles. Int J Pharm 2005; 301:149-60).

For the preparation of the macro particles, initially a primary emulsion between internal aqueous phase consisting of 2 ml MQ water and an organic phase (OP) consisting of the polymer (200 mg) dissolved in 4 ml dichloromethane was prepared by sonication (20 W, 40% duty cycle, 20 cycles), (Bandelin, Germany). The primary emulsion was dripped slowly into 300 ml of an external aqueous phase (EAP) containing the surfactant (CTAB, SDS or Tween 20) at a concentration of 1% w/v. The secondary emulsion was continuously stirred slowly overnight using a magnetic stirrer for the dichloromethane to evaporate. As the polymer particles solidify, the surfactant molecules get coated on the surface of polymer particles. Polymer micro and nano particles were prepared by varying the energy input during emulsion preparation and the OP to EAP volume ratio as described earlier (Kanchan V, Panda A K. Interactions of antigen loaded polylactide particles with macrophages and their correlation with immune response. Biomaterials 2007; 28: 5344-57). For the micro particle preparation, secondary emulsion was homogenized (10,000 rpm for 10 min) using a homogenizer (Polytron, Switzerland) and the secondary emulsion was sonicated for nano particle preparation. The resulting particles were collected by centrifugation (15,000 rpm, 20 min), and lyophilized to obtain free-flowing surfactant coated polymer particles. Polymer particles prepared with 1% (w/v) polyvinyl alcohol (PVA) in the external aqueous phase were used as control (Sahoo S K, Panda A K, Labhasetwar V. Characterization of porous PLGA/PLA microparticles as a scaffold for three dimensional growth of breast cancer cells. Biomacromolecules 2005; 6: 1132-39). Surfactant coated PLLA, PLGA and polystyrene particle were prepared using solvent evaporation method as described above. For the preparation of fluorescent particles, 50 µl of 6-coumarin dye (1 mg/ml in dichloromethane) was also added to OP during primary emulsion step (Kanchan V, Panda A K. Interactions of antigen loaded polylactide particles with macrophages and their correlation with immune response. Biomaterials 2007; 28: 5344-57). Size distribution of the particles was determined using 'Malvern mastersizer 2000' particle size analyzer (Malvern, UK).

Preparation of Polymeric Membranes and Scaffolds by Surfactant Mediated Fusion of Polymer Particles The dry surfactant coated PDLLA particles were spread on plastic petri dishes and wetted or soaked with 100% ethanol to immediately form polymeric membrane composed of fused particles. After the formation of the fused membrane, the scaffold was washed with sterile distilled water. This resulted in hardening of the membrane. By evenly spreading the polymer particles in different sized petri-dishes and fusing with ethanol spherical membrane of different dimension (desired shape, size and thickness) were fabricated. For formulating three dimensional structures, the surfactant coated particles were filled in a suitable mould (eppendorf tubes and falcon plastic tubes) and wetted with ethanol to form the shape of the mould. After the removal of ethanol and treatment with water, the three dimensional scaffolds were removed from the mold.

CTAB coated polylactide particles were spread in a Petri dish and transiently wetted with ethanol. The particles show rapid aggregation and are fused into a stable network of particles. The particle scaffold when transferred to water becomes rigid and easy to handle. The fusion of the particles occurs at room temperature. Some of the CTAB coated polylactide-co-glycolide particles do not fuse with ethanol treatment, but does so with methanol. The particles were packed in molds of desired shape and when wetted with ethanol fused in a controlled manner and on drying, stable higher order structures are obtained.

Polylactide particles coated with different surfactants like SDS and Tween 20 also showed fusion with ethanol and methanol. Normally, it is not entropically favorable for plain polylactide or polylactide-co-glycolide particles to form fusion regions when transiently wetted with ethanol or methanol.

Microscopy Analysis of the Fused Polymer Particles

The fusion bridges between the particles were visualized by using a scanning electron microscope (SEM)-model EVO 50 (Zeiss). The images were taken after coating the particle surface with gold over an aluminium stub. The Transmission electron microscopy (TEM) images of the fused micro particles were taken using CM 10, Philips, Holland after coating the particles with 1% uranyl acetate over a copper grid (Polysciences, Warrington, Pa.). Images of the fluorescent PDLLA-CTAB particles were taken using a Nikon ECLIPSE TE 2000 fluorescent microscope fitted with a digital camera (1200 DXM). Plain optical images of the fused particles were also taken under bright light in monochrome mode.

Estimation of Surfactant Desorption from the Polymer Particles During Ethanol Treatment Concentration of CTAB on the surface of the polymer particle was estimated by measuring the Zeta potential of the particles before and after treatment with ethanol using Nano Z (Malvern Instruments, UK). All the measurements of the different surfactant coated polymer particles before and after treatment with different alcohols were carried out in phosphate buffered saline (PBS). In case of scaffolds, they were broken down into fine fragments and the zeta potential value measured. The Atomic Force Microscopy (AFM) of the surfactant coated particle surface before and after ethanol treatment were carried out using Nanoscope (Veeco, USA). Particles were diluted in phosphate-buffered saline (PBS) to concentrations in the range of 0.5-2 mg/ml. The diluted solution was then deposited onto mica supports or glass slide. Amplitude-distance curves were used to optimize resolution and contrast in semi-contact mode of atomic force microscopy. A colorimetric method was employed to determine the concentration of PVA adsorbed on the PDLLA particles before and after ethanol treatment (Sahoo S K, Panyam J, Prabha S, Labhasetwar V. Residual polyvinyl alcohol associated with poly (D, L-lactide-co-glycolide) nanoparticles affects their physical properties and cellular uptake. Journal of Controlled Release 2002; 82: 105-14). PDLLA-PVA particles were treated with ethanol and the PVA concentration on the particles compared with untreated particles. Briefly, the particle samples were treated with 2 ml of 0.5 M NaOH for 15 min at 60° C. Samples were neutralized with 900 µl of 1 N HCL, and the volume was adjusted to 5 ml with distilled water. To each sample 3 ml of 0.65 M solution of boric acid, 0.5 ml of a solution of Iodine/Potassium Iodide (0.05 M/0.15 M), and 1.5 ml of distilled water were added. The absorbance of the samples was measured at 690 nm following incubation for 15 min at room temperature. Colorimetric estimation of SDS desorbed from PDLLA-SDS particles was carried before and after ethanol treatment (Arand M, Friedberg T, Oesch F. Colorimetric quantitation of trace amounts of sodium lauryl sulphate in the presence of nucleic acids and proteins. Anal Biochem 1992; 207: 73-5). The samples were transferred to an eppendorf tube and brought up to a volume of 0.3 ml by the addition of water or ethanol. An equal volume of the methylene blue reagent was added and the mixture was extracted with 1.2 ml chloroform by thorough vortexing. After centrifugation, the lower organic phase was transferred to an eppendorf tube and the absorbance of the supernatant was taken at 651 nm with chloroform as reference.

Differential Scanning Calorimetry and X-Ray Diffraction

Differential scanning calorimetry analysis of the free and fused surfactant coated particles were carried out using PYRIS 6 DSC (Perkin Elmer). The samples were heated from 35° C. to 200° C. at 10° C./min and held for 1 min at 200° C. Then the samples were cooled from 200° C. to 35° C. at 10° C./min. The X-ray diffraction of PDLLA-CTAB particles before and after ethanol treatment was carried out using PAN analytic's X'Pert X-ray diffraction system.

Evaluation of Polymer Membrane as an Artificial Skin Substitute in Animal Wound Model Animals were maintained according to the guidelines established by the Institute Animal Ethics Committee (IAEC) of the National Institute of Immunology, New Delhi. Preliminary evaluation of the polymeric membrane for wound healing was tested on Wistar rats. All surgical procedures were carried out under anesthesia. For the initial experiments, the polymeric membrane was evaluated for non-infected full skin thickness wounds (2×3 cm) on the dorsum of rats. The animals were divided into the treated and untreated groups (n=6) and in the treated group, the polymeric membrane immediately formed after the fusion process was directly transferred onto the wounds. Wound scoring was done at different time points till the complete closure of the wounds (Konrad D, Tsunoda M, Weber K, Corney S J, Ullmann L. Effects of a topical silver sulfadiazine polyurethane dressing on wound healing in experimentally infected wounds. J Exp Anim Sci 2002; 42: 31-43).

Wound Collagen Assay

The wound collagen assays of the rat's skin were performed using sircol collagen assay. The sircol collagen assay is a well established direct quantitative method for the analysis of collagens (Phillips R J, Burdick M D, Hong K, Lutz M A, Murray L A, et al. Circulating fibrocytes traffic to the lungs in response to CXCL12 and mediate fibrosis. J. Clin Invest 2004; 114: 438-46). It contains the reagent Sirius red which reacts specifically with the side chain groups of the basic amino acid groups of collagen. In brief, after an average healing period of 15 days rats (treated with polylactide membrane and the control animals) were sacrificed. The healed skin were excised and thoroughly washed with PBS. The skin was sliced into small bits; equal amounts of skin (70 mg) from both types of animals were boiled for 80° C. for 50 minutes to extract the cross-linked insoluble collagen from the healed skin of the wounds. The supernatant was filtered using 0.45 micron filters and 100 μl of the solution was added to 1 ml of the Sircol dye. After shaking for 30 minutes, the tubes were centrifuged for 5 minutes for 12,000 rpm. Unbound dye solution was drained and 1 ml of alkali reagent was added to release the unbound dye. The absorbances of the solutions were measured at 540 nm using spectrophotometer and the collagen content was calculated using a standard curve.

Example 2

Preparation of Surfactant Coated PLGA Particles and its Fusion

The polymeric particles are prepared by double emulsion solvent evaporation method. 200 mg of Polylactide-co-glycolide is dissolved in 4 ml DCM and a primary emulsion is made by sonication with an internal aqueous phase. Drugs or growth factors can be incorporated in the aqueous phase to encapsulate them in the polymeric particles. The primary emulsion was slowly dripped into an external aqueous phase (300 ml water) and stirred slowly overnight under slow stirring. The external aqueous phase contains a surfactant at a concentration of one percent. The surfactants used are CTAB, Tween 20 and SDS. The polymeric particles slowly solidify as the DCM evaporates and the surfactant molecules coat the surface of the particles. After overnight stirring the particles are washed and lyophilized to dry powder. Large porous surfactant coated polymer particles of average size 300 μm are obtained. To make smaller sized particles, the ratio between organic phase to internal aqueous phase can be varied, along with providing higher energy during secondary emulsification. CTAB coated polylactide micro and nano particles were also made by spray drying. These particles were spread on Petri dishes and wetted with methanol. The fusions of particles in to higher order structure were observed. Membrane and scaffold of different design can be formed using PLGA polymer and wetting it with methanol.

Example 3

Preparation of Polymeric Membrane in the Form of Films/Sheets

CTAB coated poly-DL-lactide particles were spread on plastic Petri dishes and gently wetted with ethanol. They showed rapid aggregation and fused into a polymeric network of particles. On transferring the polymeric membrane to water, it became rigid and was easy to handle as a sheet or membrane. Desired shape, thickness and size of the polymeric membrane can be obtained by laying out the particles as required before wetting with ethanol. The fusion of the particles occurs in a single easy step and occurs at ambient temperature. The ethanol step also effectively sterilizes the scaffold for any biomedical uses. The surfactant molecules are removed along with the ethanol, ensuring a surfactant free polymeric membrane. Presence of surfactants is detrimental to cell growth and the surfactant free scaffolds are suitable for the purpose of tissue engineering. It is seen that stable fusion regions are formed at the point of contacts between the particles, at the same time maintaining particle morphology and structure. The bulk properties of the polymer like glass transition temperature and molecular weight of the polymer are not changed during the fusion reaction with ethanol. The encapsulated proteins or growth factors are not damaged during this process. CTAB coated polylactide particles also fuse when wetted with methanol, but the fusion reaction is stronger than ethanol, with loss of particle morphology and structure. Polylactide particles coated with SDS and Tween 20 also showed fusion with ethanol and methanol. CTAB coated polylactide-co-glycolide particles fused when wetted with methanol, but not with ethanol. The phenomenon of surfactant mediated fusion of polymer particles occurred in a charge independent manner with surfactants which were positively charged (CTAB), negatively charged (SDS) and neutral in nature (Tween 20). Normally, it is not entropically favorable for polylactide to form such fusion regions in presence of ethanol or methanol, but does so in presence of organic solvents like dichloromethane, where it is soluble. It is hypothesized that it is the sudden desorption of the surfactant molecules from the surface of the polymer particles during alcohol treatment, which creates a transient local environment, where it is entropically favorable for the surface of the polymer to partly solubilize in alcohol. The evaporating ethanol phase brings the particles together and fusion regions are formed at the points of contact between the particles. The process is terminated when the surfactant molecules are dispersed into the liquid phase. This novel process of scaffold preparation is suited for various biomedical applications, as it is a controlled and gentle process which occurs at ambient temperature, thus not damaging any encapsulated factors and not changing any of the properties of the polymer. This surfactant mediated self assembly is a 'soft approach' as opposed to normal methods of fabrication which involves production of heat and friction, which will affect the particle itself in a detrimental way. The polymeric membranes composed of the fused polylactide particles are being used in wound healing in animal models.

Example 4

Stable Higher Order Scaffold Structures from Polymer Particles Using Different Moulds CTAB coated porous polylactide particles were filled in molds of different shapes like a cylinder, cube etc and wetted with ethanol. The particles rapidly fused into the shape of the mold. The three dimensional structures were removed from the molds and dried (FIG. 2). They showed good strength and stability, which are desired for scaffolds to be used in tissue engineering applications and as drug delivery implants. The porosity of the structures can be adjusted by using polymer particles of different sizes. This allows proper inflow of growth media and as a scaffold for the growing cells. Growth factors and other factors can be encapsulated in the biodegradable particles which ensure controlled release of these factors into the tissue microenvironment.

TABLE 1

Colorimetric Estimation of SDS desorption from the particles during ethanol treatment and estimation of PVA retained by the particles during water and ethanol treatment

|  | After Water Treatment (OD) | After Ethanol Treatment (OD) |
| --- | --- | --- |
| PDLLA-SDS particles | 0.098 | 0.955 |
| PDLLA-PVA particles | 0.082 | 0.071 |

What is claimed is:

1. A process of preparation of a biodegradable polymer scaffold useful for tissue engineering, therapeutic compound delivery and/or wound dressing, wherein said process comprises:
    a. adding surfactant coated polymer particles to a mold, wherein the polymer comprising said particles is selected from the group consisting of poly-DL-lactide and polylactide co-glycolide;
    b. soaking said particles with alcohol, wherein soaking causes the fusion of said particles to form a scaffold; and
    c. washing the above with water to obtain the polymer scaffold from the mold.

2. The process of preparation of the biodegradable polymer scaffold as claimed in claim 1 optionally comprising encapsulating within said polymer particles from step (a) growth factors, proteins or therapeutic compounds.

3. The process as claimed in claim 2, wherein said growth factor is selected from a group consisting of TGF-.beta family, bone morphogenic proteins, fibroblast growth factors-1 and -2, platelet-derived growth factor-AA, and -BB, platelet rich plasma, vascular endothelial cell-derived growth factor and epidermal growth factor (EGF), platelet derived growth factor (PDGF), insulin-like growth factor (IGF), basic fibroblast growth factor (bFGF), bone morphogenic proteins (BMPs) and combinations thereof.

4. The process of preparation of the biodegradable polymer scaffold as claimed in claim 1, wherein said mold is a solid support.

5. The process of preparation of the scaffold as claimed in claim 1, wherein the mold is used to shape the polymer scaffold into the shape of said mold.

6. The process as claimed in claim 1, wherein said surfactant is selected from the group consisting of cationic, anionic and neutral surfactant.

7. The process as claimed in claim 1, wherein said surfactant is selected from the group consisting of cetyl trimethyl ammonium bromide (CTAB), sodium dodecyl sulphate (SDS), and Tween 20.

8. The process as claimed in claim 1, wherein said alcohol is selected from a group consisting of ethanol, methanol and propanol.

9. The process as claimed in claim 1, wherein said alcohol is ethanol.

10. The process as claimed in claim 1, wherein said alcohol is methanol.

11. A process of preparation of a biodegradable polymer scaffold, wherein said process comprises:
    a. adding cetyl trimethyl ammonium bromide (CTAB) coated polymer particles of Poly-DL-lactide (PDLLA) to a mold;
    b. soaking said particles with ethanol or methanol, wherein soaking causes the fusion of said particles to form a scaffold; and
    c. washing the above with water to obtain the polymer scaffold from the mold.

12. A process of preparation of a biodegradable polymer scaffold, wherein said process comprises:
    a. adding cetyl trimethyl ammonium bromide (CTAB) coated polymer particles of polylactide co-glycolide particle on to a mold;
    b. soaking said particles with methanol, wherein soaking causes the fusion of said particles to form a scaffold; and
    c. washing the above with water to obtain the polymer scaffold from the mold.

13. A process of preparation of a biodegradable polymer membrane useful for tissue engineering, therapeutic compound delivery and/or wound dressing, wherein said process comprises:
    a. spreading surfactant coated polymer particles on a mold, wherein the polymer comprising said particles is selected from the group consisting of poly-DL-lactide and polylactide co-glycolide;
    b. soaking said particles with alcohol, wherein soaking causes the fusion of said particles to form a membrane; and
    c. washing the above with water to obtain the polymer membrane from the mold.

14. The process of preparation of the biodegradable polymer membrane as claimed in claim 13 optionally comprising encapsulating within said polymer particles from step (a) growth factors, proteins or therapeutic compounds.

15. The process as claimed in claim 14, wherein said growth factor is selected from a group consisting of TGF-.beta family, bone morphogenic proteins, fibroblast growth factors-1 and -2, platelet-derived growth factor-AA, and -BB, platelet rich plasma, vascular endothelial cell-derived growth factor and epidermal growth factor (EGF), platelet derived growth factor (PDGF), insulin-like growth factor (IGF), basic fibroblast growth factor (bFGF), bone morphogenic proteins (BMPs) and combinations thereof.

16. The process of preparation of the biodegradable polymer membrane as claimed in claim 13, wherein said mold is a solid support.

17. The process of preparation of the membrane as claimed in claim 13, wherein the mold is used to shape the polymer membrane into the shape of said mold.

18. The process as claimed in claim 13, wherein said surfactant is selected from the group consisting of cationic, anionic and neutral surfactant.

19. The process as claimed in claim 13, wherein said surfactant is selected from the group consisting of cetyl trimethyl ammonium bromide (CTAB), sodium dodecyl sulphate (SDS), and Tween 20.

20. The process as claimed in claim 13, wherein said alcohol is selected from a group consisting of ethanol, methanol and propanol.

21. The process as claimed in claim 13, wherein said alcohol is ethanol.

22. The process as claimed in claim 13, wherein said alcohol is methanol.

23. A process of preparation of a biodegradable polymer membrane, wherein said process comprises:
   a. spreading cetyl trimethyl ammonium bromide (CTAB) coated polymer particles of Poly-DL-lactide (PDLLA) on a mold;
   b. soaking said particles with ethanol or methanol, wherein soaking causes the fusion of said particles to form a membrane; and
   c. washing the above with water to obtain the polymer membrane from the mold.

24. A process of preparation of a biodegradable polymer membrane, wherein said process comprises:
   a. spreading cetyl trimethyl ammonium bromide (CTAB) coated polymer particles of polylactide co-glycolide particle on a mold;
   b. soaking said particles with methanol, wherein soaking causes the fusion of said particles to form a membrane; and
   c. washing the above with water to obtain the polymer membrane from the mold.

* * * * *